(12) United States Patent
Huang et al.

(10) Patent No.: US 12,174,161 B2
(45) Date of Patent: Dec. 24, 2024

(54) METHODS OF MEASURING HYDROPHOBICITY OF CHROMATOGRAPHIC RESINS

(71) Applicant: BRISTOL-MYERS SQUIBB COMPANY, Princeton, NJ (US)

(72) Inventors: Chao Huang, Devens, MA (US); Joseph James Perry, Devens, MA (US); Xuankuo Xu, Devens, MA (US); Sanchayita Ghose, Devens, MA (US); Zhengjian Li, Devens, MA (US); Weixin Jin, Devens, MA (US)

(73) Assignee: BRISTOL-MYERS SQUIBB COMPANY, Princeton, NJ (US)

( * ) Notice: Subject to any disclaimer, the term of this patent is extended or adjusted under 35 U.S.C. 154(b) by 612 days.

(21) Appl. No.: 17/599,035

(22) PCT Filed: Mar. 27, 2020

(86) PCT No.: PCT/US2020/025118
§ 371 (c)(1),
(2) Date: Sep. 28, 2021

(87) PCT Pub. No.: WO2020/205469
PCT Pub. Date: Oct. 8, 2020

(65) Prior Publication Data
US 2022/0042954 A1 Feb. 10, 2022

Related U.S. Application Data

(60) Provisional application No. 62/826,260, filed on Mar. 29, 2019.

(51) Int. Cl.
*G01N 30/50* (2006.01)
*B01D 15/32* (2006.01)
(Continued)

(52) U.S. Cl.
CPC .......... *G01N 30/50* (2013.01); *B01D 15/327* (2013.01); *B01D 15/362* (2013.01);
(Continued)

(58) Field of Classification Search
CPC .... B01D 15/00; B01D 15/327; B01D 15/361; B01D 15/362; B01D 15/3804;
(Continued)

(56) References Cited

U.S. PATENT DOCUMENTS

2019/0017977 A1* 1/2019 Rathore ................ G01N 30/89

FOREIGN PATENT DOCUMENTS

| CN | 0103282422 A1 | 9/2013 |
| CN | 00103592290 A1 | 2/2014 |

(Continued)

OTHER PUBLICATIONS

Beckley K. Nfor, et al., "Model-Based Rational Strategy for Chromatographic Resin Selection", 2011, pp. 1629-1643.
(Continued)

*Primary Examiner* — Ekandra S. Miller-Cruz
(74) *Attorney, Agent, or Firm* — Z. Angela Guo

(57) ABSTRACT

In certain embodiments, the present invention provides a method of measuring the level of hydrophobicity of a chromatographic resin. In certain embodiments, the present invention provides a method of selecting a chromatographic resin condition for purifying a protein of interest from a mixture, wherein the protein of interest has low or no aggregation formation during chromatography. In certain embodiments, the present invention provides a method of selecting a chromatographic resin from a plurality of chromatographic resins for purifying a protein of interest from a mixture, wherein the protein of interest has low or no aggregation formation during chromatography.

18 Claims, 6 Drawing Sheets

(51) Int. Cl.
*B01D 15/36* (2006.01)
*B01D 15/38* (2006.01)
*B82Y 30/00* (2011.01)
*B82Y 35/00* (2011.01)
*B82Y 40/00* (2011.01)
*C07K 1/18* (2006.01)
*C07K 1/20* (2006.01)
*G01N 30/02* (2006.01)

(52) U.S. Cl.
CPC ............ *B01D 15/3804* (2013.01); *C07K 1/18* (2013.01); *C07K 1/20* (2013.01); *B82Y 30/00* (2013.01); *B82Y 35/00* (2013.01); *B82Y 40/00* (2013.01); *G01N 2030/027* (2013.01)

(58) Field of Classification Search
CPC .... B01D 15/3847; B82Y 30/00; B82Y 35/00; B82Y 40/00; C07K 1/16; C07K 1/18; C07K 1/20; G01N 30/50; G01N 30/89; G01N 2030/027
USPC ......................................................... 210/656
See application file for complete search history.

(56) References Cited

FOREIGN PATENT DOCUMENTS

| CN | 00105860960 A1 | 8/2016 | |
|---|---|---|---|
| EP | 2918680 A1 | 5/2014 | |
| JP | 0000019115 A1 | 1/2000 | |
| WO | WO-2017011877 A1 * | 1/2017 | ............. G01N 21/64 |

OTHER PUBLICATIONS

Jie Chen, et al., "Comparison of standard and new generation hydrophobic interaction chromatography resins in the monoclonal antibody purification process", Journal of Chromatography A., 1177 (2008) 272-281.

Jordan J. Lichty, et al., "Comparison of affinity tags for protein purification", Protein Expression and Purification 41 (2005) 98-105.

* cited by examiner

METHODS OF MEASURING HYDROPHOBICITY OF CHROMATOGRAPHIC RESINS

REFERENCE TO RELATED APPLICATIONS

This application is a 371 application of PCT/US2020/025118, filed Mar. 27, 2020, which claims the priority benefit of U.S. Provisional Application No. 62/826,260, filed Mar. 29, 2019, the contents of each of which are incorporated herein by reference in their its entirety.

BACKGROUND OF THE INVENTION

The large-scale, economic purification of proteins is an increasingly important problem for the biopharmaceutical industry. Therapeutic proteins are typically produced using prokaryotic or eukaryotic cell lines that are engineered to express the protein of interest from a recombinant plasmid containing the gene encoding the protein. Separation of the desired protein from the mixture of components fed to the cells, cellular by-products, and aggregate forms of the protein, to an adequate purity, e.g., sufficient for use as a human therapeutic, poses a formidable challenge to biologics manufacturers.

Accordingly, there is a need in the art for improved protein purification methods that can be used to expedite the large-scale processing of protein-based therapeutics, such as antibodies.

SUMMARY OF THE INVENTION

In certain embodiments, the present invention provides a method of measuring the level of hydrophobicity of a chromatographic resin, comprising: (a) mixing a fluorophore with a gold nanoparticle (GNP) to form a fluorophore-conjugated gold nanoparticle; (b) contacting the fluorophore-conjugated gold nanoparticle with a chromatographic resin in a solution; (c) removing the supernatant and washing the chromatographic resin with a washing buffer; and (d) quantifying the level of fluorescence intensity of the chromatographic resin, thereby measuring the level of hydrophobicity of the chromatographic resin, wherein the level of the fluorescence intensity from (d) is indicative of the level of hydrophobicity of a chromatographic resin.

Optionally, the chromatographic resin is selected from an ion exchange chromatographic resin, a hydrophobic interaction chromatographic resin, an affinity chromatographic resin, and a mixed mode chromatographic resin.

Optionally, the fluorophore is selected from boron-dipyrromethane (BODIPY) dye, 8-anilino-1-naphthalene sulfonic acid (ANS), 4,4'-dianilino-1,1'-binaphthyl-5,5'-disulfonic acid (Bis-ANS), 6-propionyl-2-(N,N-dimethylamino)naphthalene (PRODAN), tetraphenylethene derivative, and Nile Red. Preferably, the fluorophore is boron-dipyrromethane (BODIPY) dye. Optionally, the gold nanoparticle has a diameter of 5 nm, 10 nm, 15 nm, 20 nm, 30 nm, 40 nm, 50 nm, 60 nm, 70 nm, 80 nm, 90 nm, or 100 nm. Optionally, the BODIPY is conjugated to GNP by crosslinking the NHS (N-hydroxysuccinimide) group of BODIPY NHS molecule with the primary amine group pre-attached on the GNP surface. Alternatively, the BODIPY may be conjugated to GNP using other linking chemistries including biotin-link-to-streptavidin; and maleimide-link-to-sulfhydryl.

In certain embodiments, the present invention provides a method of selecting a chromatographic resin condition for purifying a protein of interest from a mixture, wherein the protein of interest has low or no aggregation formation during chromatography, comprising: (a) mixing a fluorophore with a gold nanoparticle (GNP) to form a fluorophore-conjugated gold nanoparticle; (b) contacting the fluorophore-conjugated gold nanoparticle with a chromatographic resin in a solution under different conditions; (c) removing the supernatant and washing the chromatographic resin with a washing buffer; (d) quantifying the level of fluorescence intensity of the chromatographic resin from different conditions in (b); (e) measuring the level of hydrophobicity of the chromatographic resin under different conditions, wherein the level of the fluorescence intensity from (d) is indicative of the level of hydrophobicity of a chromatographic resin; and (f) selecting the chromatographic resin condition wherein the level of hydrophobicity of the chromatographic resin leads to low or no aggregation formation during chromatography purification of the protein of interest.

Optionally, the chromatographic resin is selected from an ion exchange chromatographic resin, a hydrophobic interaction chromatographic resin, an affinity chromatographic resin, and a mixed mode chromatographic resin.

Optionally, the fluorophore is selected from boron-dipyrromethane (BODIPY) dye, 8-anilino-1-naphthalene sulfonic acid (ANS), 4,4'-dianilino-1,1'-binaphthyl-5,5'-disulfonic acid (Bis-ANS), 6-propionyl-2-(N,N-dimethylamino)naphthalene (PRODAN), tetraphenylethene derivative, and Nile Red. Preferably, the fluorophore is boron-dipyrromethane (BODIPY) dye. Optionally, the gold nanoparticle has a diameter of 5 nm, 10 nm, 15 nm, 20 nm, 30 nm, 40 nm, 50 nm, 60 nm, 70 nm, 80 nm, 90 nm, or 100 nm. Optionally, the BODIPY is conjugated to GNP by crosslinking the NHS (N-hydroxysuccinimide) group of BODIPY NHS molecule with the primary amine group pre-attached on the GNP surface. Alternatively, the BODIPY may be conjugated to GNP using other linking chemistries including biotin-link-to-streptavidin; and maleimide-link-to-sulfhydryl.

Optionally, the protein of interest is a monoclonal antibody.

Optionally, the mixture is selected from a harvested cell culture fluid, a cell culture supernatant, and a conditioned cell culture supernatant, a cell lysate, and a clarified bulk. For example, cell culture is a mammalian cell culture (e.g., a Chinese Hamster Ovary (CHO) cell culture). Optionally, the mixture has been obtained by an affinity chromatography.

In certain embodiments, the present invention provides a method of selecting a chromatographic resin from a plurality of chromatographic resins for purifying a protein of interest from a mixture, wherein the protein of interest has low or no aggregation formation during chromatography, comprising: (a) mixing a fluorophore with a gold nanoparticle (GNP) to form a fluorophore-conjugated gold nanoparticle; (b) contacting the fluorophore-conjugated gold nanoparticle with each chromatographic resin in a solution; (c) removing the supernatant and washing the chromatographic resin with a washing buffer; (d) quantifying the level of fluorescence intensity of the chromatographic resin; (e) measuring the level of hydrophobicity of the chromatographic resin, wherein the level of the fluorescence intensity from (d) is indicative of the level of hydrophobicity of the chromatographic resin; and (f) selecting the chromatographic resin having the level of hydrophobicity which leads to low or no aggregation formation during chromatography purification of the protein of interest.

Optionally, the chromatographic resin is selected from an ion exchange chromatographic resin, a hydrophobic interaction chromatographic resin, an affinity chromatographic resin, and a mixed mode chromatographic resin.

Optionally, the fluorophore is selected from boron-dipyrromethane (BODIPY) dye, 8-anilino-1-naphthalene sulfonic acid (ANS), 4,4'-dianilino-1,1'-binaphthyl-5,5'-disulfonic acid (Bis-ANS), 6-propionyl-2-(N,N-dimethylamino)naphthalene (PRODAN), tetraphenylethene derivative, and Nile Red. Preferably, the fluorophore is boron-dipyrromethane (BODIPY) dye. Optionally, the gold nanoparticle has a diameter of 5 nm, 10 nm, 15 nm, 20 nm, 30 nm, 40 nm, 50 nm, 60 nm, 70 nm, 80 nm, 90 nm, or 100 nm. Optionally, the BODIPY is conjugated to GNP by crosslinking the NHS (N-hydroxysuccinimide) group of BODIPY NHS molecule with the primary amine group pre-attached on the GNP surface. Alternatively, the BODIPY may be conjugated to GNP using other linking chemistries including biotin-link-to-streptavidin; and maleimide-link-to-sulfhydryl.

Optionally, the protein of interest is a monoclonal antibody.

Optionally, the mixture is selected from a harvested cell culture fluid, a cell culture supernatant, and a conditioned cell culture supernatant, a cell lysate, and a clarified bulk. For example, cell culture is a mammalian cell culture (e.g., a Chinese Hamster Ovary (CHO) cell culture). Optionally, the mixture has been obtained by an affinity chromatography.

DETAILED DESCRIPTION OF THE INVENTION

Figure 1:
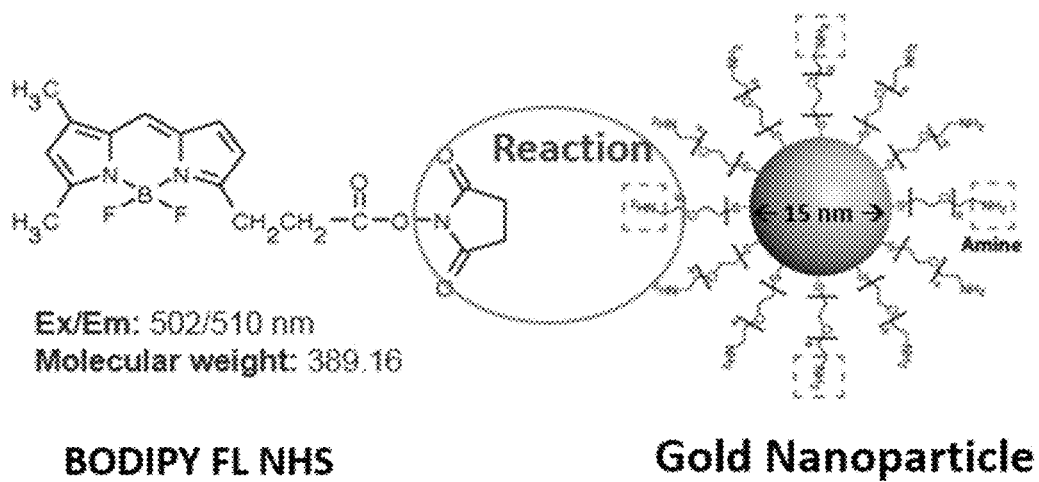
FIG. 1 shows the schematic representation of functionalizing BODIPY FL NHS onto gold nanoparticle (GNP).

In certain embodiments, the present invention provides a method of measuring the level of hydrophobicity of a chromatographic resin, comprising: (a) mixing a fluorophore with a gold nanoparticle (GNP) to form a fluorophore-conjugated gold nanoparticle; (b) contacting the fluorophore-conjugated gold nanoparticle with a chromatographic resin in a solution; (c) removing the supernatant and washing the chromatographic resin with a washing buffer; and (d) quantifying the level of fluorescence intensity of the chromatographic resin, thereby measuring the level of hydrophobicity of the chromatographic resin, wherein the level of the fluorescence intensity from (d) is indicative of the level of hydrophobicity of a chromatographic resin.

Optionally, the chromatographic resin is selected from an ion exchange chromatographic resin, a hydrophobic interaction chromatographic resin, an affinity chromatographic resin, and a mixed mode chromatographic resin.

Optionally, the fluorophore is selected from boron-dipyrromethane (BODIPY) dye, 8-anilino-1-naphthalene sulfonic acid (ANS), 4,4'-dianilino-1,1'-binaphthyl-5,5'-disulfonic acid (Bis-ANS), 6-propionyl-2-(N,N-dimethylamino)naphthalene (PRODAN), tetraphenylethene derivative, and Nile Red. Preferably, the fluorophore is boron-dipyrromethane (BODIPY) dye. Optionally, the gold nanoparticle has a diameter of 5 nm, 10 nm, 15 nm, 20 nm, 30 nm, 40 nm, 50 nm, 60 nm, 70 nm, 80 nm, 90 nm, or 100 nm. Optionally, the BODIPY is conjugated to GNP by crosslinking the NHS (N-hydroxysuccinimide) group of BODIPY NHS molecule with the primary amine group pre-attached on the GNP surface. Alternatively, the BODIPY may be conjugated to GNP using other linking chemistries including biotin-link-to-streptavidin; and maleimide-link-to-sulfhydryl.

In certain embodiments, the present invention provides a method of selecting a chromatographic resin condition for purifying a protein of interest from a mixture, wherein the protein of interest has low or no aggregation formation during chromatography, comprising: (a) mixing a fluorophore with a gold nanoparticle (GNP) to form a fluorophore-conjugated gold nanoparticle; (b) contacting the fluorophore-conjugated gold nanoparticle with a chromatographic resin in a solution under different conditions; (c) removing the supernatant and washing the chromatographic resin with a washing buffer; (d) quantifying the level of fluorescence intensity of the chromatographic resin from different conditions in (b); (e) measuring the level of hydrophobicity of the chromatographic resin under different conditions, wherein the level of the fluorescence intensity from (d) is indicative of the level of hydrophobicity of a chromatographic resin; and (f) selecting the chromatographic resin condition wherein the level of hydrophobicity of the chromatographic resin leads to low or no aggregation formation during chromatography purification of the protein of interest.

Optionally, the chromatographic resin is selected from an ion exchange chromatographic resin, a hydrophobic interaction chromatographic resin, an affinity chromatographic resin, and a mixed mode chromatographic resin.

Optionally, the fluorophore is selected from boron-dipyrromethane (BODIPY) dye, 8-anilino-1-naphthalene sulfonic acid (ANS), 4,4'-dianilino-1,1'-binaphthyl-5,5'-disulfonic acid (Bis-ANS), 6-propionyl-2-(N,N-dimethylamino)naphthalene (PRODAN), tetraphenylethene derivative, and Nile Red. Preferably, the fluorophore is boron-dipyrromethane (BODIPY) dye. Optionally, the gold nanoparticle has a diameter of 5 nm, 10 nm, 15 nm, 20 nm, 30 nm, 40 nm, 50 nm, 60 nm, 70 nm, 80 nm, 90 nm, or 100 nm. Optionally, the BODIPY is conjugated to GNP by crosslinking the NHS (N-hydroxysuccinimide) group of BODIPY NHS molecule with the primary amine group pre-attached on the GNP surface. Alternatively, the BODIPY may be conjugated to GNP using other linking chemistries including biotin-link-to-streptavidin; and maleimide-link-to-sulfhydryl.

Optionally, the protein of interest is a monoclonal antibody.

Optionally, the mixture is selected from a harvested cell culture fluid, a cell culture supernatant, and a conditioned cell culture supernatant, a cell lysate, and a clarified bulk. For example, cell culture is a mammalian cell culture (e.g., a Chinese Hamster Ovary (CHO) cell culture). Optionally, the mixture has been obtained by an affinity chromatography.

In certain embodiments, the present invention provides a method of selecting a chromatographic resin from a plurality of chromatographic resins for purifying a protein of interest from a mixture, wherein the protein of interest has low or no aggregation formation during chromatography, comprising:

(a) mixing a fluorophore with a gold nanoparticle (GNP) to form a fluorophore-conjugated gold nanoparticle; (b) contacting the fluorophore-conjugated gold nanoparticle with each chromatographic resin in a solution; (c) removing the supernatant and washing the chromatographic resin with a washing buffer; (d) quantifying the level of fluorescence intensity of the chromatographic resin; (e) measuring the level of hydrophobicity of the chromatographic resin, wherein the level of the fluorescence intensity from (d) is indicative of the level of hydrophobicity of the chromatographic resin; and (f) selecting the chromatographic resin having the level of hydrophobicity which leads to low or no aggregation formation during chromatography purification of the protein of interest.

Optionally, the chromatographic resin is selected from an ion exchange chromatographic resin, a hydrophobic interaction chromatographic resin, an affinity chromatographic resin, and a mixed mode chromatographic resin.

Optionally, the fluorophore is selected from boron-dipyrromethane (BODIPY) dye, 8-anilino-1-naphthalene sulfonic acid (ANS), 4,4'-dianilino-1,1'-binaphthyl-5,5'-disulfonic acid (Bis-ANS), 6-propionyl-2-(N,N-dimethylamino)naphthalene (PRODAN), tetraphenylethene derivative, and Nile Red. Preferably, the fluorophore is boron-dipyrromethane (BODIPY) dye. Optionally, the gold nanoparticle has a diameter of 5 nm, 10 nm, 15 nm, 20 nm, 30 nm, 40 nm, 50 nm, 60 nm, 70 nm, 80 nm, 90 nm, or 100 nm. Optionally, the BODIPY is conjugated to GNP by crosslinking the NHS (N-hydroxysuccinimide) group of BODIPY NHS molecule with the primary amine group pre-attached on the GNP surface. Alternatively, the BODIPY may be conjugated to GNP using other linking chemistries including biotin-link-to-streptavidin; and maleimide-link-to-sulfhydryl.

Optionally, the protein of interest is a monoclonal antibody.

Optionally, the mixture is selected from a harvested cell culture fluid, a cell culture supernatant, and a conditioned cell culture supernatant, a cell lysate, and a clarified bulk. For example, cell culture is a mammalian cell culture (e.g., a Chinese Hamster Ovary (CHO) cell culture). Optionally, the mixture has been obtained by an affinity chromatography.

I. Definitions

In order that the present disclosure may be more readily understood, certain terms are first defined. As used in this application, except as otherwise expressly provided herein, each of the following terms shall have the meaning set forth below. Additional definitions are set forth throughout the application.

As used herein, the term "protein of interest" is used in its broadest sense to include any protein (either natural or recombinant), present in a mixture, for which purification is desired. Such proteins of interest include, without limitation, hormones, growth factors, cytokines, immunoglobulins (e.g., antibodies), and immunoglobulin-like domain-containing molecules (e.g., ankyrin or fibronectin domain-containing molecules).

As used herein, a "cell culture" refers to cells in a liquid medium. Optionally, the cell culture is contained in a bioreactor. The cells in a cell culture can be from any organism including, for example, bacteria, fungus, insects, mammals or plants. In a particular embodiment, the cells in a cell culture include cells transfected with an expression construct containing a nucleic acid that encodes a protein of interest (e.g., an antibody). Suitable liquid media include, for example, nutrient media and non-nutrient media. In a particular embodiment, the cell culture comprises a Chinese Hamster Ovary (CHO) cell line in nutrient media, not subject to purification by, for example, filtration or centrifugation.

As used herein, the term "clarified bulk" refers to a mixture from which particulate matter has been substantially removed. Clarified bulk includes cell culture, or cell lysate from which cells or cell debris has been substantially removed by, for example, filtration or centrifugation.

As used herein, a "mixture" comprises a protein of interest (for which purification is desired) and one or more contaminant, i.e., impurities. In one embodiment, the mixture is produced from a host cell or organism that expresses the protein of interest (either naturally or recombinantly). Such mixtures include, for example, cell cultures, cell lysates, and clarified bulk (e.g., clarified cell culture supernatant).

As used herein, the terms "separating" and "purifying" are used interchangeably, and refer to the selective removal of contaminants from a mixture containing a protein of interest (e.g., an antibody).

As used herein the term "contaminant" is used in its broadest sense to cover any undesired component or compound within a mixture. In cell cultures, cell lysates, or clarified bulk (e.g., clarified cell culture supernatant), contaminants include, for example, host cell nucleic acids (e.g., DNA) and host cell proteins present in a cell culture medium. Host cell contaminant proteins include, without limitation, those naturally or recombinantly produced by the host cell, as well as proteins related to or derived from the protein of interest (e.g., proteolytic fragments) and other process related contaminants. In certain embodiments, the contaminant precipitate is separated from the cell culture using an art-recognized means, such as centrifugation, sterile filtration, depth filtration and tangential flow filtration.

As used herein "centrifugation" is a process that involves the use of the centrifugal force for the sedimentation of heterogeneous mixtures with a centrifuge, used in industry and in laboratory settings. This process is used to separate two immiscible liquids. For example, in a method of the present invention, centrifugation can be used to remove a contaminant precipitation from a mixture, including without limitation, a cell culture or clarified cell culture supernatant or capture-column captured elution pool.

As used herein "sterile filtration" is a filtration method that use membrane filters, which are typically a filter with pore size 0.2 μm to effectively remove microorganisms or small particles. For example, in a method of the present invention, sterile filtration can be used to remove a contaminant precipitate from a mixture, including without limitation, a cell culture or clarified cell culture supernatant or capture-column captured elution pool.

As used herein "depth filtration" is a filtration method that uses depth filters, which are typically characterized by their design to retain particles due to a range of pore sizes within a filter matrix. The depth filter's capacity is typically defined by the depth, e.g., 10 inch or 20 inch of the matrix and thus the holding capacity for solids. For example, in a method of the present invention, depth filtration can be used to remove a contaminant precipitate from a mixture, including without limitation, a cell culture or clarified cell culture supernatant or capture-column captured elution pool.

As used herein the term "chromatography" refers to the process by which a solute of interest, e.g., a protein of interest, in a mixture is separated from other solutes in the mixture by percolation of the mixture through an adsorbent, which adsorbs or retains a solute more or less strongly due to properties of the solute, such as pI, hydrophobicity, size and structure, under particular buffering conditions of the process. In a method of the present invention, chromatography can be used to remove contaminants after the precipitate is removed from a mixture, including without limitation, a cell culture or clarified cell culture supernatant or capture-column captured elution pool.

The terms "ion-exchange" and "ion-exchange chromatography" refer to a chromatographic process in which an ionizable solute of interest (e.g., a protein of interest in a mixture) interacts with an oppositely charged ligand linked (e.g., by covalent attachment) to a solid phase ion exchange material under appropriate conditions of pH and conductivity, such that the solute of interest interacts non-specifically with the charged compound more or less than the solute impurities or contaminants in the mixture. The contaminating solutes in the mixture can be washed from a column of the ion exchange material or are bound to or excluded from the resin, faster or slower than the solute of interest. "Ion-exchange chromatography" specifically includes cation exchange and anion exchange chromatographies.

The phrase "ion exchange material" refers to a solid phase that is negatively charged (i.e., a cation exchange resin or membrane) or positively charged (i.e., an anion exchange resin or membrane). In one embodiment, the charge can be provided by attaching one or more charged ligands (or adsorbents) to the solid phase, e.g., by covalent linking. Alternatively, or in addition, the charge can be an inherent property of the solid phase (e.g., as is the case for silica, which has an overall negative charge).

A "cation exchange resin" refers to a solid phase which is negatively charged, and which has free cations for exchange with cations in an aqueous solution passed over or through the solid phase. Any negatively charged ligand attached to the solid phase suitable to form the cation exchange resin can be used, e.g., a carboxylate, sulfonate and others as described below. Commercially available cation exchange resins include, but are not limited to, for example, those having a sulfonate based group (e.g., MonoS, MiniS, Source 15S and 30S, SP Sepharose Fast Flow™, SP Sepharose High Performance, Capto S from GE Healthcare, Toyopearl SP-650S and SP-650M from Tosoh, Macro-Prep High S from BioRad, Ceramic HyperD S, Trisacryl M and LS SP and Spherodex LS SP from Pall Technologies); a sulfoethyl based group (e.g., Fractogel SE, from EMD, Poros S-10 and S-20 from Thermo Fisher Scientific); a sulphopropyl based group (e.g., TSK Gel SP 5PW and SP-5PW-HR from Tosoh, Capto SP ImpRes from GE Healthcare, POROS HS-20, HS 50, and POROS XS from Thermo Fisher Scientific); a sulfoisobutyl based group (e.g., Fractogel EMD $SO_3^-$ from EMD); a sulfoxyethyl based group (e.g., SE52, SE53 and Express-Ion S from Whatman), a carboxymethyl based group (e.g., CM Sepharose Fast Flow from GE Healthcare, Hydrocell CM from Biochrom Labs Inc., Macro-Prep CM from BioRad, Ceramic HyperD CM, Trisacryl M CM, Trisacryl LS CM, from Pall Technologies, Matrx Cellufine C500 and C200 from Millipore, CM52, CM32, CM23 and Express-Ion C from Whatman, Toyopearl CM-650S, CM-650M and CM-650C from Tosoh); sulfonic and carboxylic acid based groups (e.g., BAKERBOND Carboxy-Sulfon from J.T. Baker); a carboxylic acid based group (e.g., WP CBX from J.T Baker, DOWEX MAC-3 from Dow Liquid Separations, Amberlite Weak Cation Exchangers, DOWEX Weak Cation Exchanger, and Diaion Weak Cation Exchangers from Sigma-Aldrich and Fractogel EMD COO— from EMD); a sulfonic acid based group (e.g., Hydrocell SP from Biochrom Labs Inc., DOWEX Fine Mesh Strong Acid Cation Resin from Dow Liquid Separations, UNOsphere S, WP Sulfonic from J. T. Baker, Sartobind S membrane from Sartorius, Amberlite Strong Cation Exchangers, DOWEX Strong Cation and Diaion Strong Cation Exchanger from Sigma-Aldrich); and a orthophosphate based group (e.g., P11 from Whatman).

An "anion exchange resin" refers to a solid phase which is positively charged, thus having one or more positively charged ligands attached thereto. Any positively charged ligand attached to the solid phase suitable to form the anionic exchange resin can be used, such as quaternary amino groups Commercially available anion exchange resins include DEAE cellulose, POROS PI 20, PI 50, HQ 10, HQ 20, HQ 50, D 50, and POROS XQ from Thermo Fisher Scientific, Sartobind Q from Sartorius, MonoQ, MiniQ, Source 15Q and 30Q, Q, DEAE and ANX Sepharose Fast Flow, Q Sepharose high Performance, Capto Q, QAE SEPHADEX™ and FAST Q SEPHAROSE™ (GE Healthcare), WP PEI, WP DEAM, WP QUAT from J.T. Baker, Hydrocell DEAE and Hydrocell QA from Biochrom Labs Inc., UNOsphere Q, Macro-Prep DEAE and Macro-Prep High Q from Biorad, Ceramic HyperD Q, ceramic HyperD DEAE, Trisacryl M and LS DEAE, Spherodex LS DEAE, QMA Spherosil LS, QMA Spherosil M and Mustang Q from Pall Technologies, DOWEX Fine Mesh Strong Base Type I and Type II Anion Resins and DOWEX MONOSPHER E 77, weak base anion from Dow Liquid Separations, Intercept Q membrane, Matrex Cellufine A200, A500, Q500, and Q800, from Millipore, Fractogel EMD TMAE, Fractogel EMD DEAE and Fractogel EMD DMAE from EMD, Amberlite weak strong anion exchangers type I and II, DOWEX weak and strong anion exchangers type I and II, Diaion weak and strong anion exchangers type I and II, Duolite from Sigma-Aldrich, TSK gel Q and DEAE 5PW and 5PW-HR, Toyopearl SuperQ-650S, 650M and 650C, QAE-550C and 650S, DEAE-650M and 650C from Tosoh, QA52, DE23, DE32, DE51, DE52, DE53, Express-Ion D and Express-Ion Q from Whatman, and Sartobind Q (Sartorius corporation, New York, USA).

A "mixed mode ion exchange resin" or "mixed mode" refers to a solid phase which is covalently modified with cationic, anionic, and/or hydrophobic moieties. Examples of mixed mode ion exchange resins include BAKERBOND ABX' (J. T. Baker; Phillipsburg, NJ), ceramic hydroxyapatite type I and II and fluoride hydroxyapatite (BioRad; Hercules, CA), MEP and MBI HyperCel (Pall Corporation; East Hills, NY), Capto adhere, Capto MMC and Capto MMC ImpRes (GE Healthcare)

A "hydrophobic interaction chromatography resin" refers to a solid phase which is covalently modified with methyl, ether, phenyl, butyl, hexyl, and octyl chemicals. Hydrophobic interaction chromatography is a separation technique that uses the properties of hydrophobicity to separate proteins from one another. In this type of chromatography, hydrophobic groups such as, methyl, ether, phenyl, butyl, hexyl, and octyl are attached to the stationary column. Proteins that pass through the column that have hydrophobic amino acid side chains on their surfaces are able to interact with and bind to the hydrophobic groups on the column. Examples of hydrophobic interaction chromatography resins include: (1) Butyl FF, Butyl HP, Octyl FF, Phenyl FF, Phenyl HP, Phenyl FF (high sub), Phenyl FF (low sub), Capto Phenyl ImpRes, Capto Phenyl (high sub), Capto Octyl, Capto Butyl ImpRes, Capto Butyl (GE Healthcare, Uppsala, Sweden); (2) Toyopearl Super Butyl-550C, Toyopearl Hexyl-650C, Butyl-650C, Phenyl-650C, Butyl 600 M, Phenyl-600M, PPG-600M, Butyl-650M, Phenyl-650M, Ether-650M, Butyl-650S, Phenyl-650S, Ether-650S, TSKgel Pheny-5PW, TSKgel Ether-5PW (Tosoh Bioscience, Tokyo, Japan); (3) Macro-Prep-butyl, Macro-Prep-methyl (Bio-Rad); (4) Sartobind Phenyl (Sartorius corporation, New York, USA), and (5) POROS Ethyl, POROS Benzyl, POROS Benzyl Ultra (Thermo Fisher Scientific)

II. Proteins of Interest

In certain aspects, methods of the present invention may be used to purify any protein of interest including, but not limited to, proteins having pharmaceutical, diagnostic, agricultural, and/or any of a variety of other properties that are useful in commercial, experimental or other applications. In addition, a protein of interest can be a protein therapeutic. In certain embodiments, proteins purified using methods of the present invention may be processed or modified. For example, a protein of interest in accordance with the present invention may be glycosylated.

Thus, the present invention may be used to culture cells for production of any therapeutic protein, such as pharmaceutically or commercially relevant enzymes, receptors, receptor fusion proteins, antibodies (e.g., monoclonal or polyclonal antibodies), antigen-binding fragments of an antibody, Fc fusion proteins, cytokines, hormones, regulatory factors, growth factors, coagulation/clotting factors, or antigen-binding agents. The above list of proteins is merely exemplary in nature, and is not intended to be a limiting recitation. One of ordinary skill in the art will know that other proteins can be produced in accordance with the present invention, and will be able to use methods disclosed herein to produce such proteins.

In one particular embodiment of the invention, the protein purified using the method of the invention is an antibody. The term "antibody" is used in the broadest sense to cover monoclonal antibodies (including full length monoclonal antibodies), polyclonal antibodies, multispecific antibodies (e.g., bispecific antibodies), antibody fragments, immunoadhesins and antibody-immunoadhesin chimerias.

An "antibody fragment" includes at least a portion of a full length antibody and typically an antigen binding or variable region thereof. Examples of antibody fragments include Fab, Fab', F(ab')$_2$, and Fv fragments; single-chain antibody molecules; diabodies; linear antibodies; and multispecific antibodies formed from engineered antibody fragments.

The term "monoclonal antibody" is used in the conventional sense to refer to an antibody obtained from a population of substantially homogeneous antibodies such that the individual antibodies comprising the population are identical except for possible naturally occurring mutations that may be present in minor amounts. Monoclonal antibodies are highly specific, being directed against a single antigenic site. This is in contrast with polyclonal antibody preparations which typically include varied antibodies directed against different determinants (epitopes) of an antigen, whereas monoclonal antibodies are directed against a single determinant on the antigen. The term "monoclonal", in describing antibodies, indicates the character of the antibody as being obtained from a substantially homogeneous population of antibodies, and is not to be construed as requiring production of the antibody by any particular method. For example, monoclonal antibodies used in the present invention can be produced using conventional hybridoma technology first described by Kohler et al., Nature 256:495 (1975), or they can be made using recombinant DNA methods (see, e.g., U.S. Pat. No. 4,816,567). Monoclonal antibodies can also be isolated from phage antibody libraries, e.g., using the techniques described in Clackson et al., Nature 352:624-628 (1991); Marks et al., J. Mol. Biol. 222:581-597 (1991); and U.S. Pat. Nos. 5,223,409; 5,403,484; 5,571,698; 5,427,908 5,580,717; 5,969,108; 6,172,197; 5,885,793; 6,521,404; 6,544,731; 6,555,313; 6,582,915; and 6,593,081).

The monoclonal antibodies described herein include "chimeric" and "humanized" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., Proc. Natl. Acad. Sci. USA 81:6851-6855 (1984)). "Humanized" forms of non-human (e.g., murine) antibodies are chimeric antibodies which contain minimal sequence derived from non-human immunoglobulin. For the most part, humanized antibodies are human immunoglobulins (recipient antibody) in which the hypervariable region residues of the recipient are replaced by hypervariable region residues from a non-human species (donor antibody) such as mouse, rat, rabbit or nonhuman primate having the desired specificity, affinity, and capacity. In some instances, Fv framework region (FR) residues of the human immunoglobulin are replaced by corresponding non-human residues. Furthermore, humanized antibodies may comprise residues which are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence. The humanized antibody optionally also will comprise at least a portion of an immunoglobulin constant region (Fc), typically that of a human immunoglobulin. For further details, see Jones et al., Nature 321:522-525 (1986); Riechmann et al., Nature 332:323-329 (1988); and Presta, Curr. Op. Struct. Biol. 2:593-596 (1992).

Chimeric or humanized antibodies can be prepared based on the sequence of a murine monoclonal antibody prepared as described above. DNA encoding the heavy and light chain immunoglobulins can be obtained from the murine hybridoma of interest and engineered to contain non-murine (e.g., human) immunoglobulin sequences using standard molecular biology techniques. For example, to create a chimeric antibody, the murine variable regions can be linked to human constant regions using methods known in the art (see e.g., U.S. Pat. No. 4,816,567 to Cabilly et al.). To create a humanized antibody, the murine CDR regions can be inserted into a human framework using methods known in the art (see e.g., U.S. Pat. No. 5,225,539 to Winter, and U.S. Pat. Nos. 5,530,101; 5,585,089; 5,693,762 and 6,180,370 to Queen et al.).

The monoclonal antibodies described herein also include "human" antibodies, which can be isolated from various sources, including, e.g., from the blood of a human patient or recombinantly prepared using transgenic animals. Examples of such transgenic animals include KM-Mouse® (Medarex, Inc., Princeton, NJ) which has a human heavy chain transgene and a human light chain transchromosome (see WO 02/43478), Xenomouse® (Abgenix, Inc., Fremont CA; described in, e.g., U.S. Pat. Nos. 5,939,598; 6,075,181; 6,114,598; 6, 150,584 and 6,162,963 to Kucherlapati et al.), and HuMAb-Mouse® (Medarex, Inc.; described in, e.g., Taylor, L. et al. (1992) *Nucleic Acids Research* 20:6287-6295; Chen, J. et al. (1993) *International Immunology* 5: 647-656; Tuaillon et al. (1993) *Proc. Natl. Acad. Sci. USA* 90:3720-3724; Choi et al. (1993) *Nature Genetics* 4:117-123; Chen, J. et al. (1993) *EMBO J.* 12: 821-830; Tuaillon et al. (1994) *J. Immunol.* 152:2912-2920; Taylor, L. et al. (1994) *International Immunology* 6: 579-591; and Fishwild, D. et al. (1996) *Nature Biotechnology* 14: 845-851, U.S. Pat. Nos. 5,545,806; 5,569,825; 5,625,126; 5,633,425; 5,789, 650; 5,877,397; 5,661,016; 5,814,318; 5,874,299; and 5,770,429; 5,545,807; and PCT Publication Nos. WO 92/03918, WO 93/12227, WO 94/25585, WO 97/13852, WO 98/24884 and WO 99/45962, WO 01/14424 to Korman et al.). Human monoclonal antibodies of the invention can also be prepared using SCID mice into which human immune cells have been reconstituted such that a human antibody response can be generated upon immunization. Such mice are described in, for example, U.S. Pat. Nos. 5,476,996 and 5,698,767 to Wilson et al.

III. Mixtures Containing a Protein of Interest

The methods of the invention can be applied to any mixture containing a protein of interest. In one embodiment, the mixture is obtained from or produced by living cells that express the protein to be purified (e.g., naturally or by genetic engineering). Optionally, the cells in a cell culture include cells transfected with an expression construct containing a nucleic acid that encodes a protein of interest. Methods of genetically engineering cells to produce proteins are well known in the art. See e.g., Ausabel et al., eds. (1990), Current Protocols in Molecular Biology (Wiley, New York) and U.S. Pat. Nos. 5,534,615 and 4,816,567, each of which are specifically incorporated herein by reference. Such methods include introducing nucleic acids that encode and allow expression of the protein into living host cells. These host cells can be bacterial cells, fungal cells, insect cells or, preferably, animal cells grown in culture. Bacterial host cells include, but are not limited to *E. coli* cells. Examples of suitable *E. coli* strains include: HB101, DH5α, GM2929, JM109, KW251, NM538, NM539, and any *E. coli* strain that fails to cleave foreign DNA. Fungal host cells that can be used include, but are not limited to, *Saccharomyces cerevisiae*, *Pichia pastoris* and *Aspergillus* cells. Insect cells that can be used include, but are not limited to, *Bombyx mori*, *Mamestra drassicae*, *Spodoptera frupperda*, *Trichoplusia ni*, *Drosophilia melanogaster*.

A number of mammalian cell lines are suitable host cells for expression of proteins of interest. Mammalian host cell lines include, for example, COS, PER.C6, TM4, VERO076, DXB11, MDCK, BRL-3A, W138, Hep G2, MMT, MRC 5, FS4, CHO, 293T, A431, 3T3, CV-1, C3H10T1/2, Colo205, 293, HeLa, L cells, BHK, HL-60, FRhL-2, U937, HaK, Jurkat cells, Rat2, BaF3, 32D, FDCP-1, PC12, M1x, murine myelomas (e.g., SP2/0 and NS0) and C2C12 cells, as well as transformed primate cell lines, hybridomas, normal diploid cells, and cell strains derived from in vitro culture of primary tissue and primary explants. New animal cell lines can be established using methods well known by those skilled in the art (e.g., by transformation, viral infection, and/or selection). Any eukaryotic cell that is capable of expressing the protein of interest may be used in the disclosed cell culture methods. Numerous cell lines are available from commercial sources such as the American Type Culture Collection (ATCC). In one embodiment of the invention, the cell culture, e.g., the large-scale cell culture, employs hybridoma cells. The construction of antibody-producing hybridoma cells is well known in the art. In one embodiment of the invention, the cell culture, e.g., the large-scale cell culture, employs CHO cells to produce the protein of interest such as an antibody (see, e.g., WO 94/11026). Various types of CHO cells are known in the art, e.g., CHO-K1, CHO-DG44, CHO-DXB11, CHO/dhfr⁻ and CHO-S.

In certain embodiments, the present invention contemplates, prior to purifying a protein of interest from a cell culture, monitoring particular conditions of the growing cell culture. Monitoring cell culture conditions allows for determining whether the cell culture is producing the protein of interest at adequate levels. For example, small aliquots of the culture are periodically removed for analysis in order to monitor certain cell culture conditions. Cell culture conditions to be monitored include, but not limited to, temperature, pH, cell density, cell viability, integrated viable cell density, lactate levels, ammonium levels, osmolality, and titer of the expressed protein. Numerous techniques are well known to those of skill in the art for measuring such conditions/criteria. For example, cell density may be measured using a hemocytometer, an automated cell-counting device (e.g., a Coulter counter, Beckman Coulter Inc., Fullerton, Calif.), or cell-density examination (e.g., CEDEX®, Innovatis, Malvern, Pa.). Viable cell density may be determined by staining a culture sample with Trypan blue. Lactate and ammonium levels may be measured, e.g., with the BioProfile 400 Chemistry Analyzer (Nova Biomedical, Waltham, Mass.), which takes real-time, online measurements of key nutrients, metabolites, and gases in cell culture media. Osmolality of the cell culture may be measured by, e.g., a freezing point osmometer. HPLC can be used to determine, e.g., the levels of lactate, ammonium, or the expressed protein. In one embodiment of the invention, the levels of expressed protein can be determined by using, e.g., protein A HPLC. Alternatively, the level of the expressed protein can be determined by standard techniques such as Coomassie staining of SDS-PAGE gels, Western blotting, Bradford assays, Lowry assays, biuret assays, and UV absorbance. Optionally, the present invention may include monitoring the post-translational modifications of the expressed protein, including phosphorylation and glycosylation.

In a specific embodiment, methods of the present invention comprise effectively removing contaminants from a mixture (e.g., a cell culture, cell lysate or clarified bulk) which contains a high concentration of a protein of interest (e.g., an antibody). For example, the concentration of a protein of interest may range from about 0.5 to about 50 mg/ml (e.g., 0.5, 1, 5, 10, 15, 20, 25, 30, 35, 40, 45 or 50 mg/ml).

Preparation of mixtures initially depends on the manner of expression of the protein. Some cell systems directly secrete the protein (e.g., an antibody) from the cell into the surrounding growth media, while other systems retain the antibody intracellularly. For proteins produced intracellularly, the cell can be disrupted using any of a variety of methods, such as mechanical shear, osmotic shock, and enzymatic treatment. The disruption releases the entire contents of the cell into the homogenate, and in addition produces subcellular fragments which can be removed by centrifugation or by filtration. A similar problem arises, although to a lesser extent, with directly secreted proteins due to the natural death of cells and release of intracellular host cell proteins during the course of the protein production run.

In one embodiment, cells or cellular debris are removed from the mixture, for example, to prepare clarified bulk. The methods of the invention can employ any suitable methodology to remove cells or cellular debris. If the protein is produced intracellularly, as a first step, the particulate debris, either host cells or lysed fragments, can be removed, for example, by a centrifugation or filtration step in order to prepare a mixture which is then subjected to purification according the methods described herein (i.e., from which a protein of interest is purified). If the protein is secreted into the medium, the recombinant host cells may be separated from the cell culture medium by, e.g., centrifugation, tangential flow filtration or depth filtration, in order to prepare a mixture from which a protein of interest is purified.

In another embodiment, cell culture or cell lysate is used directly without first removing the host cells. Indeed, the methods of the invention are particularly well suited to using mixtures comprising a secreted protein and a suspension of host cells.

The present disclosure is further illustrated by the following examples, which should not be construed as further limiting. The contents of all figures and all references, patents and published patent applications cited throughout this application are expressly incorporated herein by reference in their entireties.

Example 1

The method herein describes a technique to characterize the overall hydrophobicity of chromatographic resins using gold nanoparticles functionalized with fluorescent dyes. Currently, retention time measurement of small globular model proteins (e.g., ribonuclease A, lysozyme) is the standard approach to compare the hydrophobicity of adsorbents, particularly for hydrophobic interaction chromatography (HIC) resins (*GE Healthcare, Certificate of Analysis of Phenyl Sepharose™ 6 Fast Flow (high sub), Test and Limits: AS* 45-6003-91 *Ed. AG* 3). However, a general method to quantify resin hydrophobicity for a broad range of chromatography types is still lacking and highly desirable. Fluorescent dyes for measuring surface hydrophobicity have been employed to characterize the lumped hydrophobic property of cation exchange chromatography (CEX) resins (Chen Z, Huang C, Chennamsetty N, Xu X, Li Z J. *J Chromatogr A.* 2016, 1460:110-122). Due to the small size of the dye (usually <1000 Dalton) used, the probed hydrophobic resin surface is not equally accessible to the larger biologics proteins (usually >10,000 Dalton). In addition, the charge property of fluorescent dyes can also influence the resin hydrophobicity test and complicate the results. Thus, in this method, we prepared a new probe by functionalizing BODIPY FL NHS (a hydrophobicity-sensing fluorescent dye with no charge) onto gold nanoparticles (GNP). BODIPY FL emits fluorescent signal in non-polar (hydrophobic) environment (Dorh N, Zhu S, Dhungana K B, Pati R, Luo F T, Liu H, Tiwari A. *Sci Rep.* 2015; 5: 18337.), while GNP provides steric hindrance similar to that of the target biomacromolecules (e.g., monoclonal antibodies, mAbs) (Robertson J, Rizzello L, Avila-Olias M, Gaitzsch J, Contini C, Magoń M, Renshaw S, and Battagliab G, *Sci Rep.* 2016; 6: 27494.). GNP-BODIPY conjugate was prepared by cross-linking the NHS (N-hydroxysuccinimide) group of BODIPY FL NHS molecule with the primary amine group pre-attached on the GNP surface. The data showed that the new probe is able to quantify the overall hydrophobicity of HIC and CEX resins with a potential similar application to other resin types such as anion exchange chromatography (AEX), affinity chromatography (AC) and mixed mode chromatography (MM) resins. This method can be optimized for more applications. For example, the steric hindrance effect can be adjusted by using GNPs of different sizes to measure the accessible resin surface hydrophobicity for various target molecules.

A schematic representation of functionalizing BODIPY FL NHS onto gold nanoparticle (GNP) is shown in FIG. 1.

Figure 2:
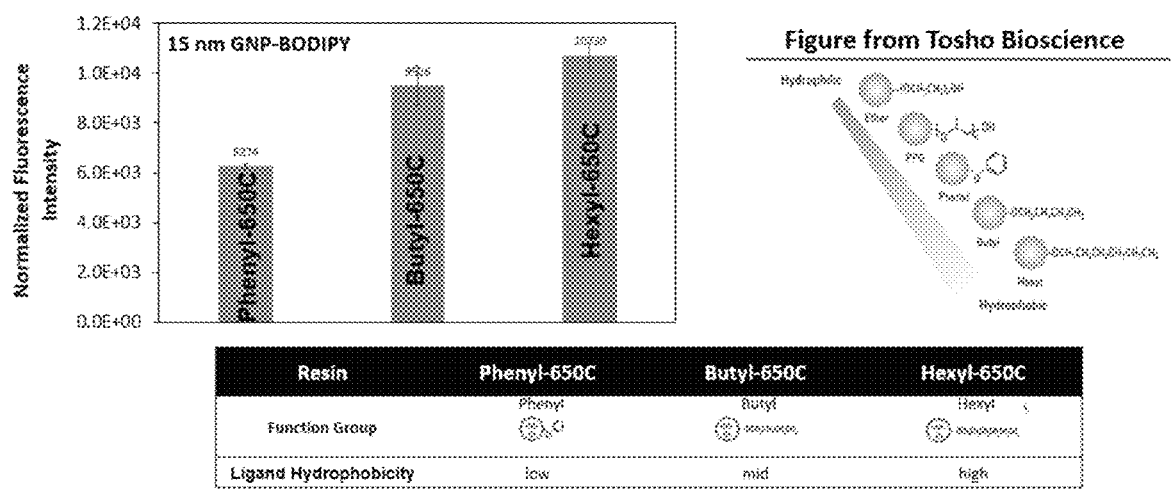
FIG. 2 shows the hydrophobicity ranking of HIC resins by the GNP-BODIPY method.

In the first experiment, Applicants demonstrated that this method was able to quantify the overall hydrophobicity of HIC resins. The hydrophobicity ranking (Hexyl-650C>Buty-650C>Phenyl-650C) by the GNP-BODIPY method agrees well with that claimed by the resin vendor. See FIG. 2.

Figure 3:
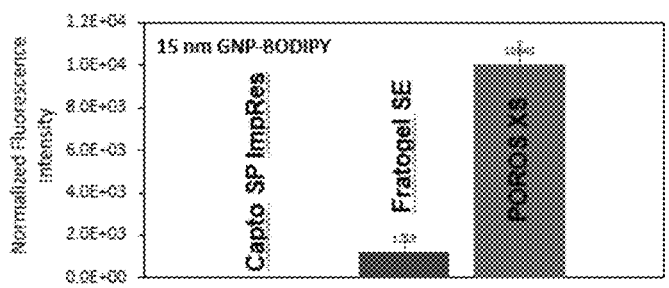
FIG. 3 shows the hydrophobicity ranking of CEX resins by the GNP-BODIPY method.

In the second experiment, Applicants demonstrated that this method was able to quantify the overall hydrophobic property of CEX resins. The GNP-BODIPY method ranked the hydrophobicity of CEX resins (POROS XS>Fractogel SE>Capto SP ImpRes) from various vendors. See FIG. 3.

Figure 4:
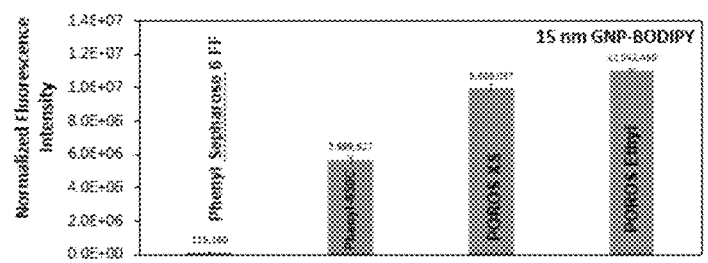
FIG. 4 shows the hydrophobicity from different base matrix materials by the GNP-BODIPY method.

In the third experiment, Applicants demonstrated that this method was used to compare the overall hydrophobic property specifically for resins (both CEX and HIC) made with different base matrix materials. See FIG. 4.

Figure 5:
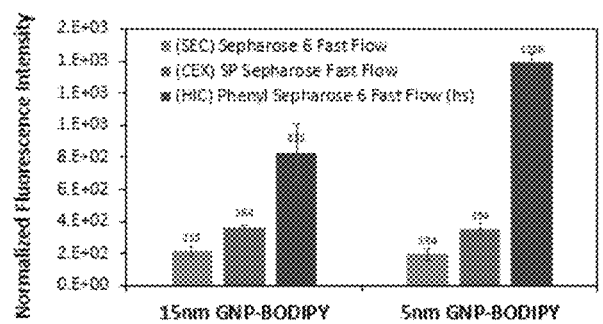
FIG. 5 shows the impact of GNP size on accessible hydrophobicity for various resin types.

In the fourth experiment, Applicants demonstrated that the GNP size (i.e., diameter) was used as an adjustable parameter to probe steric hindrance effect and its impact on accessible hydrophobicity for chromatographic resins. See FIG. 5.

Next, Applicants performed the following experiments with practical significance.

A. Chromatography Process Development

This tool facilitates the chromatography (especially polishing steps) process development and parameter optimization. The hydrophobic property of CEX resins plays a critical role through the impact on product quality of the therapeutic proteins (e.g., mAbs). For example, depending on the resin and solution conditions used, IgG1 and IgG4 mAbs can form high molecular weight (HMW) aggregates across the CEX step operated either in bind/elute or flow/through mode. Resin surface hydrophobicity that is accessible to the bound IgG molecules was found to be in good correlation with the mAb aggregation propensity in the CEX step. The tool developed here can be used to aid the development and optimization of the CEX process that achieves optimal column performance and product quality.

Figure 6:
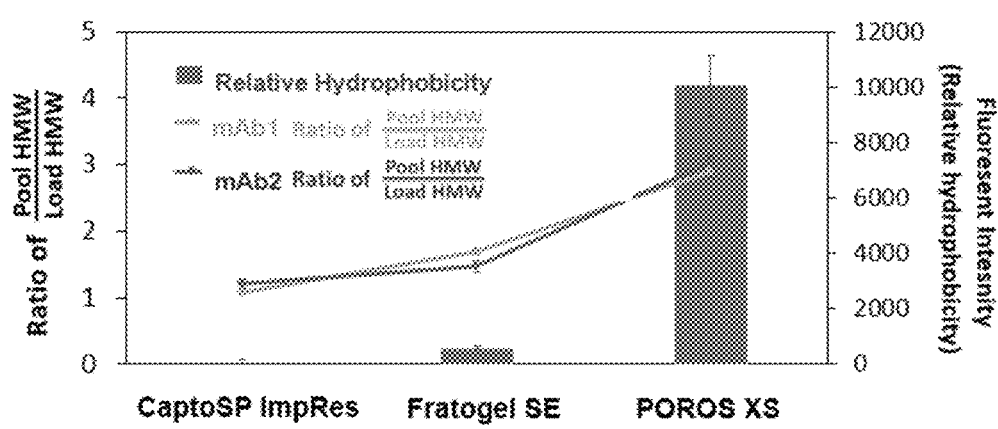
FIG. 6 shows the impact of resin hydrophobic surface accessible to bound mAb molecules. mAb1 is a IgG1, and mAb2 is a IgG4. The ratio of pool HMW and load HMW indicates aggregation formation. Ratio >1 suggests on-column aggregation.

FIG. 6 shows the impact of resin hydrophobic surface accessible to bound mAb molecules. mAb1 is a IgG1, and mAb2 is a IgG4. The ratio of pool HMW and load HMW indicates aggregation formation. Ratio>1 suggests on-column aggregation.

B. Resin Hydrophobicity Assay Independent of Chromatography Types

The assay requires simple procedure and very small sample quantities for resin. It offers adequate sensitivity that can be used to compare the hydrophobic properties of broad range of resins, regardless of chromatography types (e.g., HIC, CEX, AEX, MM, AC, etc.). Using the instructions described here, resin overall hydrophobicity can be quantified using ~50 μL resin (settled volume) within 60 minutes run time.

An example of resin hydrophobicity testing protocol is shown below.

1. Prepare 100 μL with 50% resin slurry in 25 mM NaAcetate, pH 5.5 buffer

2. Add 5 µL of 100 µL GNP-BODIPY stock to target 10 pg BODIPY per µL settled resin
3. Add 25 mM NaAcetate, pH 5.5 buffer to final 500 µL
4. Invert mixing for 30 min and centrifuge at 5000×g for 1 min
5. Remove supernatant and add 1 mL of 25 mM NaAcetate, pH 5.5 to invert mixing for 10 min
6. Centrifuge at 5000×g for 3 min, and remove supernatant completely
7. Add 50 µL of 25 mM NaAcetate, pH 5.5 buffer to the resin
8. Transfer resin slurry into Uni cuvette (Unchained lab, Cat. No: 201-1009), and use filter paper to remove extra liquid
9. Use original resin slurry (without GNP-BODIPY) as negative control
10. Place Uni cuvette on platform of ChemiDoc XRS+ (BioRad, Cat. No: 1708265) instrument
11. Open Image Lab software (BioRad, Cat. No: 1708265) and select Fluorescein as filter
12. Obtain fluorescent intensity data by exposure for 0.1 to 1.0 second
13. Plot normalized fluorescent intensity (sample data minus negative control data) of each resin to obtain relative hydrophobicity.

EQUIVALENTS

Those skilled in the art will recognize or be able to ascertain using no more than routine experimentation, many equivalents of the specific embodiments of the invention described herein. Such equivalents are intended to be encompassed by the following claims.

INCORPORATION BY REFERENCE

All patents, pending patent applications, and other publications cited herein are hereby incorporated by reference in their entireties.

We claim:

1. A method of measuring a level of hydrophobicity of a chromatographic resin, comprising:
   (a) mixing a fluorophore with a gold nanoparticle (GNP) to form a fluorophore-conjugated gold nanoparticle;
   (b) contacting the fluorophore-conjugated gold nanoparticle with a chromatographic resin in a solution;
   (c) removing a supernatant and washing the chromatographic resin with a washing buffer; and
   (d) quantifying a level of fluorescence intensity of the chromatographic resin,
   thereby measuring the level of hydrophobicity of the chromatographic resin, wherein the level of the fluorescence intensity from (d) is indicative of the level of hydrophobicity of a chromatographic resin.

2. The method of claim 1, wherein the chromatographic resin is selected from an ion exchange chromatographic resin, a hydrophobic interaction chromatographic resin, an affinity chromatographic resin, and a mixed mode chromatographic resin.

3. The method of claim 1, wherein the fluorophore is selected from boron-dipyrromethane (BODIPY) dye, 8-anilino-1-naphthalene sulfonic acid (ANS), 4,4'-dianilino-1,1'-binaphthyl-5,5'-disulfonic acid (Bis-ANS), 6-propionyl-2-(N,N-dimethylamino) naphthalene (PRODAN), tetraphenylethene derivative, and Nile Red.

4. The method of claim 3, wherein the fluorophore is boron-dipyrromethane (BODIPY) dye.

5. The method of claim 1, wherein the gold nanoparticle has a diameter of 5 nm, 10 nm, 15 nm, 20 nm, 30 nm, 40 nm, 50 nm, 60 nm, 70 nm, 80 nm, 90 nm, or 100 nm.

6. The method of claim 4, wherein the BODIPY is conjugated to GNP by crosslinking the NHS (N-hydroxysuccinimide) group of BODIPY NHS molecule with the primary amine group pre-attached on the GNP surface.

7. A method of selecting a chromatographic resin condition for purifying a protein of interest from a mixture, wherein the protein of interest has a low or no aggregation formation during chromatography, comprising:
   (a) mixing a fluorophore with a gold nanoparticle (GNP) to form a fluorophore-conjugated gold nanoparticle;
   (b) contacting the fluorophore-conjugated gold nanoparticle with a chromatographic resin in a solution under different conditions;
   (c) removing a supernatant and washing the chromatographic resin with a washing buffer;
   (d) quantifying a level of fluorescence intensity of the chromatographic resin from different conditions in (b);
   (e) measuring a level of hydrophobicity of the chromatographic resin under different conditions, wherein the level of the fluorescence intensity from (d) is indicative of the level of hydrophobicity of a chromatographic resin; and
   (f) selecting the chromatographic resin condition based on the level of hydrophobicity of the chromatographic resin which leads to the low or no aggregation formation during chromatography purification of the protein of interest.

8. A method of selecting a chromatographic resin from a plurality of chromatographic resins for purifying a protein of interest from a mixture, wherein the protein of interest has a low or no aggregation formation during chromatography, comprising:
   (a) mixing a fluorophore with a gold nanoparticle (GNP) to form a fluorophore-conjugated gold nanoparticle;
   (b) contacting the fluorophore-conjugated gold nanoparticle with each chromatographic resin of the plurality of chromatographic resins in a solution;
   (c) removing a supernatant and washing each chromatographic resin of the plurality of chromatographic resins with a washing buffer;
   (d) quantifying a level of fluorescence intensity of each chromatographic resin of the plurality of chromatographic resins;
   (e) measuring a level of hydrophobicity of each chromatographic resin of the plurality of chromatographic resins, wherein the level of the fluorescence intensity from (d) is indicative of the level of hydrophobicity of each chromatographic resin of the plurality of chromatographic resins; and
   (f) selecting the chromatographic resin of the plurality of chromatographic resins having the level of hydrophobicity which leads to the low or no aggregation formation during chromatography purification of the protein of interest.

9. The method of claim 7, wherein the protein of interest is a monoclonal antibody.

10. The method of claim 7, wherein the chromatography is cation exchange chromatography (CEX).

11. The method of claim 7, wherein the mixture has been obtained by an affinity chromatography.

12. The method of claim 7, wherein the mixture is selected from a harvested cell culture fluid, a cell culture supernatant, and a conditioned cell culture supernatant, a cell lysate, and a clarified bulk.

13. The method of claim 12, wherein the cell culture of the harvested cell culture fluid or the cell culture supernatant or the conditioned cell culture supernatant is a mammalian cell culture.

14. The method of claim 13, wherein the cell culture of the harvested cell culture fluid or the cell culture supernatant or the conditioned cell culture supernatant is a Chinese Hamster Ovary (CHO) cell culture.

15. The method of claim 8, wherein the protein of interest is a monoclonal antibody.

16. The method of claim 8, wherein the chromatography is cation exchange chromatography (CEX).

17. The method of claim 8, wherein the mixture e has been obtained by an affinity chromatography.

18. The method of claim 8, wherein the mixture is selected from a harvested cell culture fluid, a cell culture supernatant, and a conditioned cell culture supernatant, a cell lysate, and a clarified bulk.

\* \* \* \* \*